(12) United States Patent
Verma

(10) Patent No.: US 11,660,437 B2
(45) Date of Patent: May 30, 2023

(54) HEMOSTASIS VALVE

(71) Applicant: Penumbra, Inc., Alameda, CA (US)

(72) Inventor: Vinita Verma, Pleasanton, CA (US)

(73) Assignee: PENUMBRA, INC., Alameda, CA (US)

( * ) Notice: Subject to any disclaimer, the term of this patent is extended or adjusted under 35 U.S.C. 154(b) by 13 days.

(21) Appl. No.: 17/243,810

(22) Filed: Apr. 29, 2021

(65) Prior Publication Data

US 2021/0370038 A1    Dec. 2, 2021

Related U.S. Application Data

(60) Provisional application No. 63/030,150, filed on May 26, 2020.

(51) Int. Cl.
*A61M 39/06* (2006.01)
*A61F 2/95* (2013.01)

(52) U.S. Cl.
CPC ........... *A61M 39/0606* (2013.01); *A61F 2/95* (2013.01); *A61F 2/9517* (2020.05); *A61M 2207/00* (2013.01)

(58) Field of Classification Search
CPC ........ A61M 39/0606; A61M 2039/062; A61M 2039/0626; A61M 39/0613
See application file for complete search history.

(56) References Cited

U.S. PATENT DOCUMENTS

| | | | |
|---|---|---|---|
| 5,125,903 A * | 6/1992 | McLaughlin | A61M 39/0606 137/849 |
| 5,195,980 A | 3/1993 | Catlin | |
| 5,254,097 A | 10/1993 | Schock et al. | |
| 5,273,546 A | 12/1993 | McLaughlin et al. | |
| 5,324,271 A * | 6/1994 | Abiuso | A61M 39/0613 604/167.03 |
| 6,994,700 B2 | 2/2006 | Elkins et al. | |
| 7,901,379 B2 | 3/2011 | Argentine et al. | |
| 2006/0036218 A1 | 2/2006 | Goodson et al. | |
| 2017/0361083 A1 | 12/2017 | Sutton | |

OTHER PUBLICATIONS

PCT Invitation to Pay Additional Fees for International Application No. PCT/US2021/029813, dated Jul. 28, 2021 (2 pages).
PCT International Search Report for International Application No. PCT/US2021/029813, dated Oct. 5, 2021 (12 pages).

\* cited by examiner

*Primary Examiner* — Julian W Woo
(74) *Attorney, Agent, or Firm* — Haley Guiliano LLP

(57) ABSTRACT

A hemostasis valve for use with catheters in intravascular procedures. The hemostasis valve comprising a sealable fluid channel that bifurcates from a single distal lumen to two proximal lumens. An upper proximal lumen may include a funnel shaped opening to improve aspiration potential. Rotating locking mechanisms are attachable at the ends of the hemostasis valve to interlock coaxial devices or to form seals around coaxial devices. Injection molding may be used to manufacture a hemostasis valve and its components. A mold and core pins may impart external and internal shapes to a molten polymer. Once the polymer has cooled, the molded component is separated from any pins or molds and attached to other molded components to form an assembled hemostasis valve.

6 Claims, 7 Drawing Sheets

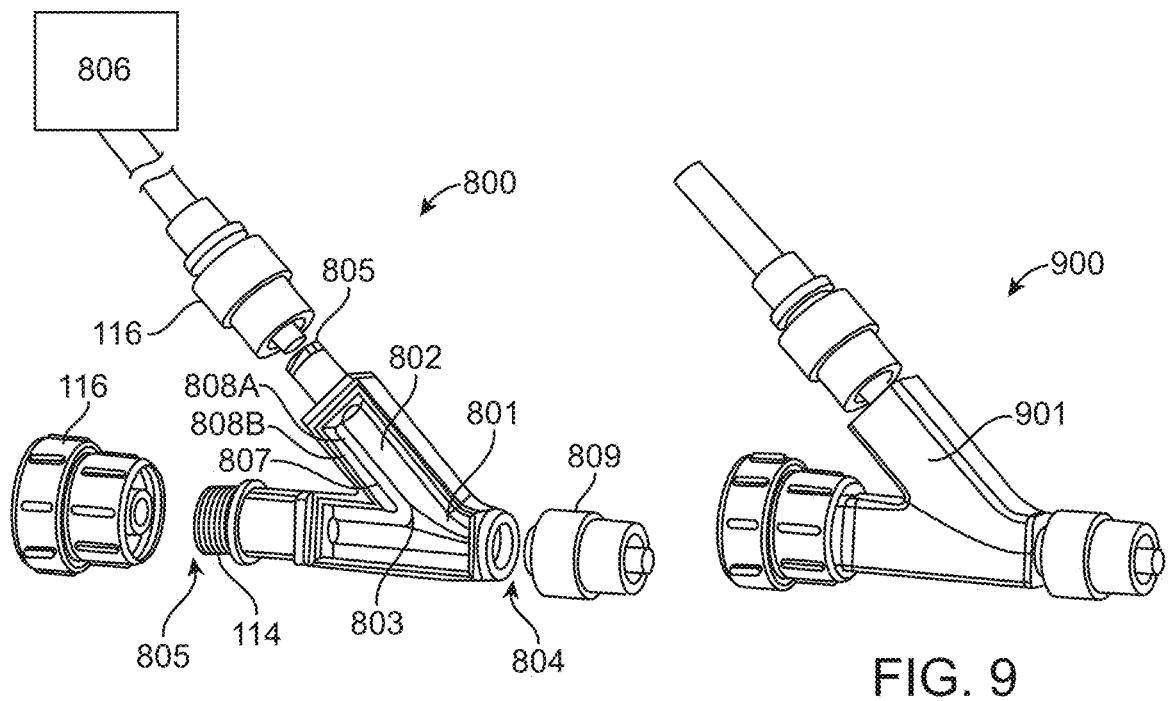
FIG. 8
FIG. 9
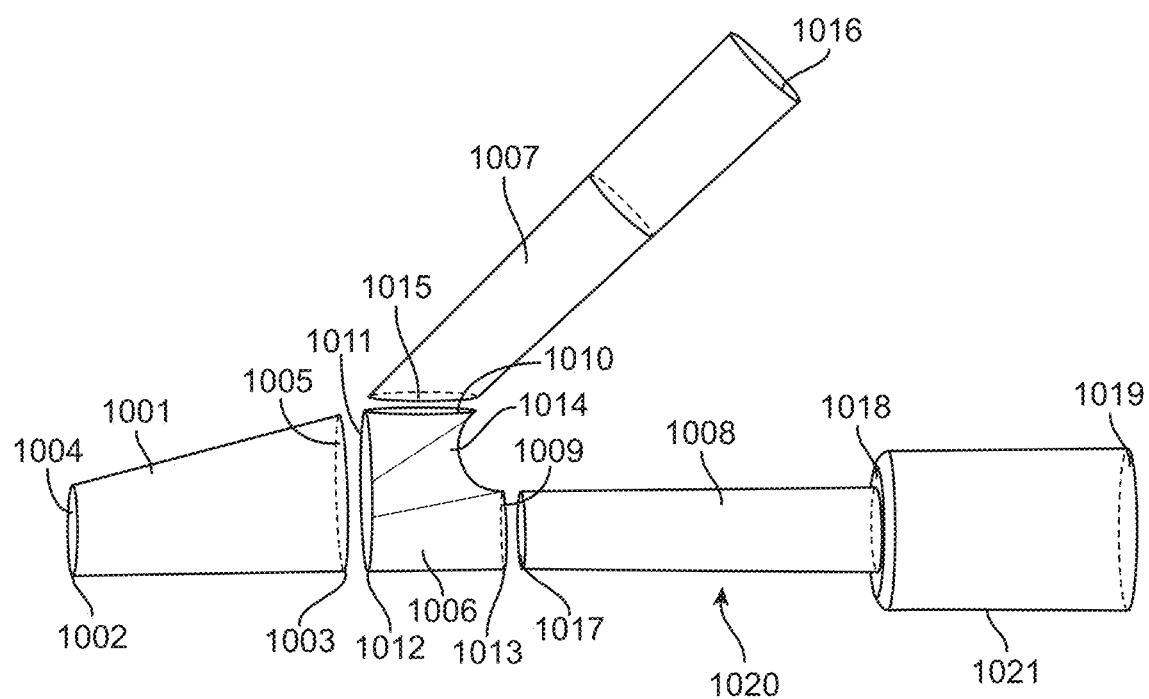
FIG. 10

HEMOSTASIS VALVE

CROSS REFERENCE TO RELATED APPLICATION

This disclosure claims the benefit of commonly-assigned U.S. Provisional Patent Application No. 63/030,150, filed May 26, 2020, which is hereby incorporated by reference herein in its entirety.

BACKGROUND OF THE INVENTION

The present disclosure relates to interventional devices and systems, methods of their manufacture and use, and, more particularly, to hemostasis valves that maintain hemostasis during introduction, use, and withdrawal of diagnostic and interventional devices.

Interventional procedures provide minimally invasive, image-guided diagnosis and treatment of diseases. Interventional procedures often utilize catheters to deliver embolic coils, stents, filters, or the like, or to provide fluid or aspiration. Catheters are typically attached to or passed through a hemostasis valve, which helps establish a closed system during interventional procedures.

A hemostasis valve establishes a common conduit between any number of interventional devices. For instance, a catheter may be attached to an end of a hemostasis valve and then smaller catheters, guidewires, and other similar devices can be passed through both the hemostasis valve and the attached catheter to reach a target in a patient's body lumen or vasculature. The hemostasis valve includes pliable seals that form around the exterior surface of inserted devices to create a closed system that minimizes fluid loss and avoids air embolisms during interventional and diagnostic procedures.

Interventional procedures are often utilized to remove blood clots responsible for diseases such as stroke and deep vein thrombosis. In some cases, blood clots are removed by advancing a reperfusion catheter to the clot and then applying aspiration to the catheter. Blood clots are often large and fibrous and are best removed by the largest catheter that can be successfully introduced into the clogged vessel. Such catheters may have an effective cross-sectional area that is larger than those of available hemostasis valves. When aspirating through such large catheters, the size, internal geometry, and flow path of ordinary hemostasis valves may present a bottleneck in the aspiration system that presents a clogging risk and can reduce the removal potential of the clot. The present disclosure addresses at least some of these issues.

SUMMARY

The present disclosure describes a hemostasis valve having lumens with optimized geometries. The hemostasis valve is typically placed on a proximal end or region of a catheter or guidewire, whereby it facilitates a closed system that prevents blood loss and air embolism. Preferably, the effective cross-sectional area of every lumen is similar to or greater than 10F in diameter.

One embodiment of the hemostasis valve comprises a linear fluid channel including a lumen extending between a proximal end and a distal end; an angled channel having a lumen extending between a proximal end and, disposed more distally, an opening into the linear channel; and wherein the opening includes a distal side disposed near or immediately adjacent to the distal end of the linear channel and a proximal side disposed at an intermediate point along the linear fluid channel. The distal side of the opening may include at least two angled transitions into the opening of the angled channel. The distal side of the opening may include a first angled transition positioned immediately after a lumen of a distal rotating locking mechanism. The distal side of the opening may include a second angled transition positioned immediately after a proximal end of a distal locking mechanism. The proximal side of the opening may include a setback bifurcation surface. The proximal side of the opening may be positioned at an intersection between the angled lumen and the linear lumen. The intersection may be set back and may provide a rounded surface between the angled lumen and the linear lumen. The opening of the angled channel may comprise of a diagonal and tapered side wall thereby creating a funnel section.

In some embodiments, the linear fluid channel of the hemostasis valve may be configured to accommodate sealed insertion of catheters and guidewires. The linear fluid channel may be configured to accommodate sealed insertion of catheters and guidewires. The hemostasis valve may be configured to couple with one or more rotating locking mechanisms.

Some embodiments of the hemostasis valve may comprise a sealable fluid channel that bifurcates from a single distal channel to two proximal channels; and a bifurcation surface formed between the two proximal channels includes a setback from an intersection point of the two proximal channels. The bifurcation surface between the two proximal channels may have a round shape. The bifurcation surface between the two proximal channels may have a hyperbolic paraboloid shape. One of the proximal channels may include a funnel section. At least one of the two proximal channels may include a compartment for seals that are configured to enclose around any inserted catheters or guidewires. The single distal channel may include an outer surface with one or more annular ridges that accommodate rotating locking mechanisms. The single distal channel may include distal, intermediary, and proximal ridges that are at least semi-annular. The intermediary and proximal ridges may form an annular recession configured to accommodate a floating latch. At least one of the two proximal channels may include proximally positioned threads on an outer surface. At least one of the two proximal channels may include an annular ledge to constrain the movement of a proximal rotating locking mechanism. The ledge may be at least semi-annular and may wrap around at least a portion of a circumference of the outer surface of the proximal channel. The ledge may be square edged, rounded-square edged, polygonal edged, or fin edged. The hemostasis valve may include a proximal rotating locking mechanism, wherein the proximal rotating locking mechanism includes an inner surface with threads that are proximally disposed and internally facing, a proximal ledge immediately distal to the threads, and a distal ledge. The distal ledge and the proximal edge may be at least semi-annular, wherein they wrap around a perimeter of the inner surface of the proximal rotating locking mechanism. The distal ledge may be flat and squared on a proximal side and sloped and rounded on a distal side. The proximal ledge may be flat and squared on a distal side. Every channel may be 10F in diameter or greater throughout. The distal and intermediary annular ridges may be fully annular, and the proximal annular ridge may be only partial annular. A distal rotating locking mechanism may have seats for at least the distal and intermediary annular ridges, wherein the seats and annular ridges have a consistent interface distance that permits smooth rotation of the distal rotating locking mechanism over the annular ridges. The distal rotating locking mechanism may include a floating latch on a proximal end.

A further embodiment of the hemostasis valve may comprise a single distal lumen that bifurcates into two proximal lumens; a first fluid channel and a second fluid channel in sealed connection, wherein the first fluid channel includes a portion of the distal lumen and the second fluid channel includes a remainder of the distal lumen and the two proximal lumens; and an intersection between the two proximal lumens is set back and a surface of the intersection is rounded. The surface of the intersection may have a hyperbolic paraboloid shape. The first channel may include either a protrusion or a cavity and the second channel may include the mating side of the protrusion or cavity. The first channel may be fixedly attached to the second channel via the protrusion and cavity. The cavity may be at least semi-annular in shape. The cavity may include a squared-edged bottom and a variable depth. The protrusion may include a peg that extends further than the rest of the protrusion. The protrusion and cavity may be complimentary in shape and only fit together in a single orientation. The first fluid channel may include an exterior surface with two or more annular ridges. The first fluid channel may include an exterior surface with distal, intermediary, and proximal annular ridges. The hemostasis valve may include a distal rotating locking mechanism having seats for at least the distal and intermediary annular ridges, wherein the seats and annular ridges have a consistent interface distance that permits smooth rotation of the distal rotating locking mechanism over the annular ridges. The lumens may be configured to accommodate the insertion of catheters and guidewires. At least one lumen may include a compartment for seals that are configured to enclose around an inserted catheters or guidewires. The hemostasis valve may be configured to accommodate one or more rotating locking mechanisms.

One embodiment of a method of manufacturing a hemostasis valve may comprise the steps of: positioning a hyperbolic paraboloid pin, an upper pin, and a linear pin at least partially into a first mold, whereby the pins form a portion of a distal lumen that bifurcates into two proximal lumens and a bifurcation surface that is set back from an intersection point between the two proximal lumens; heating a first polymer until it is partially or completely molten; pouring the partially or completely molten first polymer into the first mold; allowing the first polymer to cool until hardened; removing hyperbolic paraboloid pin, the upper pin, and the linear pin; and removing a first molded polymer from the first mold. The method may include the step of positioning an interface of the linear pin against a first interface of the hyperbolic paraboloid pin and positioning an interface of the upper pin against a second interface of the hyperbolic paraboloid pin, whereby two interfaces form a seal that excludes molten polymer and forms a continuous lumen between two pins. The bifurcation surface may have a hyperbolic paraboloid shape. One of the two proximal lumens may include at least a portion of a funnel section. The first mold may include a mating feature to interlock with a second molded polymer. The first mold may include an at least semi-annular cavity with a circumference that surrounds an outer perimeter of a distal side the portion of the distal lumen.

One embodiment of a method of manufacturing a hemostasis valve may include the steps of: positioning a tapered pin into a second mold, whereby the tapered pin forms a remaining portion of the distal lumen with a smaller distal opening and a larger proximal opening; heating a second polymer until it is partially or completely molten; pouring the partially or completely molten second polymer into the first mold; allowing the second polymer to cool until hardened; removing the tapered pin; removing a second molded polymer from the second mold; and adhering the second molded polymer to the first molded polymer. The first mold may include a groove to form an annular ridge around an outer surface of the two proximal lumens, wherein the ridge is squared on one side and rounded on another side. The first mold may include an at least semi-annular indent with a circumference that surrounds an outer perimeter of the portion of distal lumen. The second mold may include grooves to form three at least semi-annular ridges that wrap around a perimeter of the tapered lumen. The at least semi-annular protrusion may include a square peg that protrudes further than the rest of the protrusion. The at least semi-annular protrusion of the second mold may be complimentary in shape to the at least semi-annular ident of the first mold. The larger proximal opening of the second mold may be complimentary in size and shape to an opening of the single distal lumen of the first mold. One of the two proximal lumens may include a first portion of a funnel section and the distal lumen may include a second portion of the funnel section. The first portion and the second portion of the funnel section may comprise of two or more angled transitions. The funnel section may comprise the bifurcation surface that is set back on one side and the first portion and the second portion on an opposite side. The second mold may include a mating feature to interlock with the first molded polymer. The second mold may include an at least semi-annular protrusion with a circumference that surrounds an outer perimeter of a distal side of the remaining portion of the distal lumen. The protrusion may be configured to interlock with the cavity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 8 illustrates an exploded clamshell hemostasis valve.

FIG. 9 illustrates an assembled clamshell hemostasis valve.

FIG. 10 illustrates core pins used for injection molding.

DETAILED DESCRIPTION OF THE INVENTION

The present disclosure may be best understood through the following detailed description and the related illustrations. In this description, like numbers refer to similar elements within various embodiments of the present disclosure. Within this detailed description, the claimed description will be explained with respect to preferred embodiments. However, a person having ordinary skill in the art will readily appreciate that the systems, methods, and devices described herein are merely exemplary and that variations can be made without departing from the spirit and scope of the disclosure.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

Some aspects of the present disclosure are presented as a series of steps. Any particular order of steps is merely illustrative of one possible order. It should be understood that steps may be skipped, steps may be combined, steps may be divided, and the order of the steps may be varied without departing from the spirit and scope of the disclosure.

Figure 1:
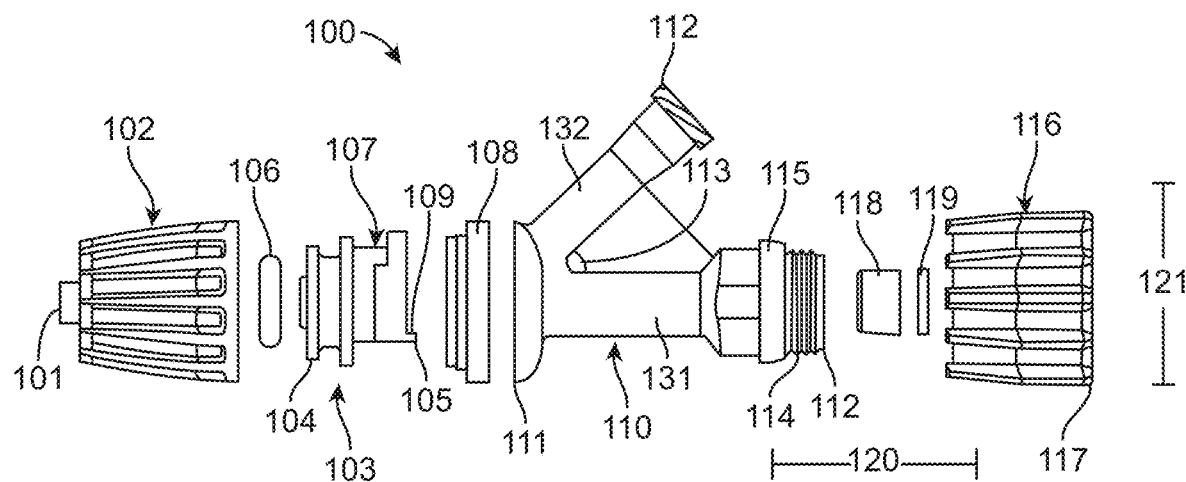
FIG. 1 illustrates an exploded hemostasis valve and optional accessories.

FIG. 1 provides an illustration of an exploded hemostasis valve 100, where individual components are separated from neighboring components by some distance. The distal end 101 of the exploded hemostasis valve 100 may include a distal rotating locking mechanism 102 with external ridges and grooves that facilitate grip by a user's fingers when the distal rotating locking mechanism 102 is rotated or otherwise manipulated. The distal rotating locking mechanism 102 may attach a hub of a catheter to an assembled hemostasis valve 200, whereby a continuous lumen is created between the catheter and the assembled hemostasis valve 200. The exploded hemostasis valve 100 preferably includes a first fluid channel 103 with a distal end 104 and a proximal end 105, which forms a portion of the lumen of an assembled hemostasis valve 200. An O-ring 106 may provide an airtight seal between the first fluid channel 103 and the distal rotating locking mechanism 102. The O-ring 106 may have a shape resembling a torus. The first fluid channel 103 may include an annular recession 107 that accommodates the placement of a floating latch 108. The floating latch 108 may provide an interface between the distal rotating locking mechanism 102 and the first fluid channel 103 to facilitate a connection of the two structures. The first fluid channel 103 may include a protrusion 109 or other similar feature to facilitate connection to an indent 304 (not shown here) of a second fluid channel 110. In alternative embodiments, the first fluid channel 103 may include an indent or a feature to facilitate connection to a protrusion or a mating feature of the second fluid channel 110 (not illustrated). In either case, the indent, the protrusion, or mating feature and the like may be at least semi-annular in shape and have a key and lock relation, whereby they only fit together in one orientation. In a further alternative, the fluid channels may be connected by a corner joint, a lap joint, a T-joint, an edge joint, a dovetail joint, a tongue and groove joint, or two flat surfaces and a butt-joint. These features help ensure that the first fluid channel 108 and the second fluid channel 110 are connected in an air-tight and a proper orientation.

The second fluid channel 110 includes a single channel at a distal end 111 and two channels at both proximal ends 112. The two proximal channels may be described as a linear channel 131 and an angled channel 132. The linear channel 131 may be a primary channel that is a continuation of and axially aligned with at least a portion of the single distal channel of the second fluid channel 110 and the first fluid channel 103. The angled channel 132 may be a secondary or auxiliary channel. Typically, aspiration is attached to one of the two proximal channels and coaxial devices are inserted through the other channel. In one example, aspiration is attached to the angled channel 132 and coaxial devices are inserted through the linear channel 131, whereby the coaxial devices may be advanced through the linear channel 131, the single channel at the distal end 111 of the second fluid channel 110, through the first fluid channel 103, and out of the distal locking mechanism 102.

The angled channel 132 may be disposed at an angle relative to the first fluid channel 103 and the linear channel 131. Alternatively, the two proximal channels may be orientated at an angle 113 relative to one another. The angle 113 may be between 15 and 75 degrees. An angle that is too acute, e.g. less than 15 degrees, would require a longer device to both produce a rounded corner at the bifurcation and to attach a locking mechanism that can spin without hitting the adjacent channel. These concerns may limit the usability of the device and undesirably increase the overall footprint of the device. On the other hand, if the angle was too large, e.g. greater than 75 degrees, then the aspiration flow path would become more tortuous and pressure drops would occur as the flow loses kinetic energy when traversing a steep redirection of the flow path.

The second fluid channel 110 may include threads 114 and a ledge 115 on an outer surface. The relative position and the shape of threads 114 and the ledge 115 may facilitate precision tightening and loosening of a proximal rotating locking mechanism 116 axially over the second fluid channel 110. The threads 114 may be positioned immediately adjacent to one of the proximal ends 112. The ledge 115 may be positioned near one of the proximal ends 112 and may be positioned immediately distal to the threads 114. The ledge 115 may have an at least semi-annular perimeter that wraps around the outer circumference of the second fluid channel 110. The ledge 115 may have edges that are squared or have a rounded-square shape. The ledge 115 may have a cross-section that is squared, curved, polygonal, fin-shaped, or some other similar shape. The shape of the ledge 115 may affect how it interacts with the proximal locking mechanism 116. For instance, a steep surface may cause abrupt stops in axial translation, while curved or rounded surfaces may facilitate more gradual restrictions to axial translation. In one embodiment, the ledge 115 has a greater height on a distal side and slopes to a shorter height on a proximal side. The slope may be sectional and comprised of two or more distinct angles. In one example, a distal slope is less steep and a proximal slope is more steep. In a fin-edged example, the ledge 115 may have a generally squared distal side and a smooth curve from the top of the distal side all the way to the bottom of the proximal side. In this sense, the ledge 115 has a cross-section resembling a fin's shape. In some examples, the ledge 115 is flat and squared on a distal side and sloped and rounded on a proximal side. The ledge 115 may function to prevent overtightening and over-loosening of a proximal rotating locking mechanism 116. The proximal rotating locking mechanism 116 may include external ridges and grooves that facilitate grip by a user's fingers when the proximal rotating locking mechanism 116 is rotated or otherwise manipulated. The proximal rotating locking mechanism 116 may have a proximal end 117 that defines the proximal end of an assembled hemostasis valve 200.

At an interface between the proximal rotating locking mechanism 116 and the second fluid channel 110 may be a seal 118 and a seal stabilizer 119, which facilitate a closed system by sealing around devices inserted through the hemostasis valve. The seal 118 and the seal stabilizer 119 may include compressible lumens that match the size and geometry of the lumens of the second fluid channel 110 when uncompressed. When in use, coaxial devices, such as catheters and guidewires, may be passed through the second fluid channel 110 and the proximal rotating locking mechanism 116 may be tightened, whereby the seal 118, the seal stabilizer 119, or both are compressed to create a seal around any inserted devices to create a closed system. Even in the absence of an inserted device, the seal 118 and the seal stabilizer 119 may be compressed by the proximal rotating locking mechanism 110 to seal on themselves and create a closed system. The seal 118 and seal stabilizer 119 may have a shape that resembles a flattened torus or a torus with flat surfaces and squared edges or rounded-squared edges. The exploded hemostasis valve 100, and every other hemostasis valve disclosed herein, has a length 120 and a width 121, as indicated by the bars bearing those element numbers.

Figure 2:
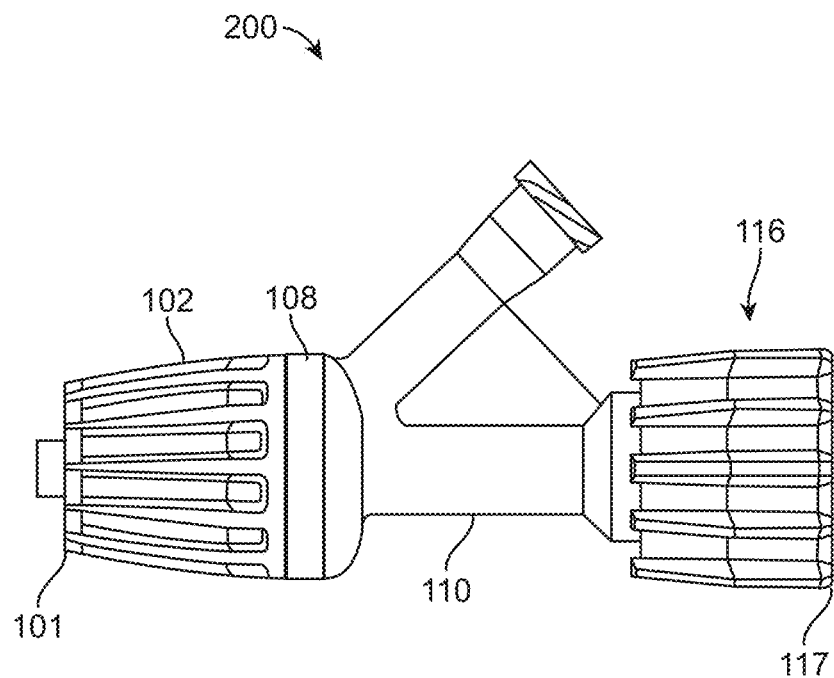
FIG. 2 illustrates an assembled hemostasis valve.

FIG. 2 provides an illustration of an assembled hemostasis valve 200, which is sealable with the proper attachments, such as catheters, connective tubing, guidewires, and the like. The distal end 101 of the hemostasis valve 200 is optionally delineated by the distal rotating locking mechanism 102. The distal rotating locking mechanism 102 may be fixedly attached to the floating latch 108, which spins freely over the first fluid channel (not visible) and spins adjacent to the second fluid channel 110, which may remain stationary. The distal rotating locking mechanism 102 may be spun to attach, via threads 302, a hub of a catheter to a distal end 101 of the assembled hemostasis valve 200. The second fluid channel 110 may include threads 114 that facilitate the attachment of devices that provide access, fluid, or aspiration to body lumens and vasculature of a patient. The proximal end 117 of the hemostasis valve 200 is optionally delineated by the proximal rotating locking mechanism 116. The proximal rotating locking mechanism 116 may advance towards a center of the assembled hemostasis valve 200 when it is tightened and may retract away from the center of the assembled hemostasis valve 200 when it is loosened. As the proximal rotating locking mechanism 116 is tightened, any seals within the second fluid channel 110 may be compressed to create a closed system.

Figure 3:
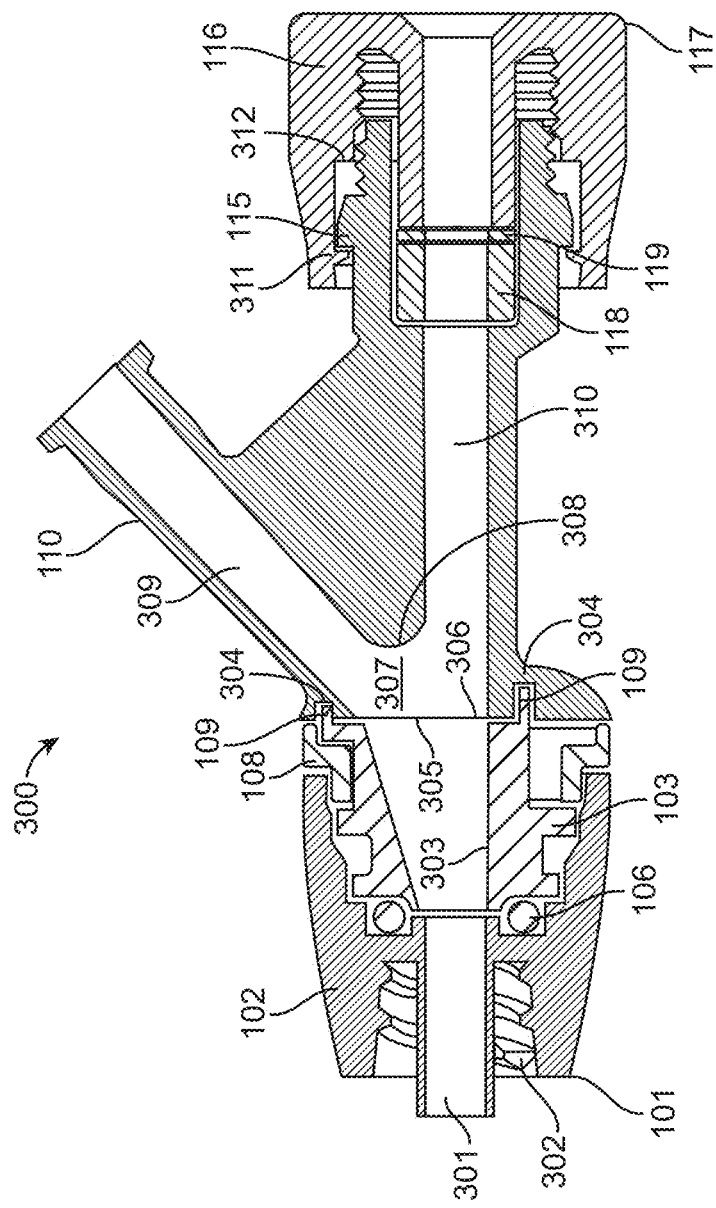
FIG. 3 illustrates an assembled, cross-sectioned hemostasis valve.

FIG. 3 provides an illustration of a cross-sectioned, assembled hemostasis valve 300. From this perspective the lumen 301 of the distal rotating locking mechanism 102 is visible. This lumen 301 is smooth on both an inner and outer surface and is preferably sized to match or be larger than an attachable catheter that forms a seal with lumen 301 after it is spun into threads 302 of the distal rotating locking mechanism 102. The threads 302 of the distal rotating locking mechanism 102 may be positioned on an inner surface of the distal rotating locking mechanism 102 and may be inwardly facing. The first fluid channel 103 may include a tapered lumen 303 that has a smaller distal diameter or smaller distal effective cross-sectional area and a larger proximal diameter or a larger proximal effective cross-sectional area. In this example, the first fluid channel 103 includes a protrusion 109 or feature that mates with an indent 304 or feature of the second fluid channel 110, e.g. mating features. The indent 304 or feature may be at least semi-annular in shape. These complimentary mating features of the first fluid channel 103 and the second fluid channel 110 may facilitate a closed system by ensuring that they are attached to one another in a proper orientation. The first fluid channel 103 typically includes a proximal opening 305 that is sized to match a single distal opening 306 of the second fluid channel 110, whereby a smooth and continuous lumen is formed between the first fluid channel 103 and the second fluid channel 110. As illustrated in FIG. 3, the proximal opening 305 has a larger effective cross-sectional area in a region adjacent to the single distal opening 306 than a region adjacent to the distal end of the first fluid channel 103. That is, proximal opening 305 tapers from its proximal side (adjacent to single distal opening 306) to its distal side (adjacent to the distal end of the first fluid channel 103). The second fluid channel typically includes a single lumen 307 in a distal region of the second fluid channel 110, an internal bifurcation 308 from one to two fluid channels, wherein the internal bifurcation 308 presents a round and smooth edge between the two fluid channels, and the two fluid channels typically comprise of an upper lumen 309 and a linear lumen 310 that both extend towards the proximal ends 112 of the second fluid channel 110. In other examples, the second fluid channel 110 may bifurcate into two angled lumens. The cross-sectioned assembled hemostasis valve 300 may be viewed as a whole, as having a lumen extending from the proximal end 101 to the distal end 117. This lumen may be truncated by removing the rotating locking mechanisms on each end. This lumen may be generally linear apart from an intersection with an angled lumen. The angled lumen may have an opening into the linear lumen, where the opening has a proximal side and a distal side. The opening may have a shape resembling a funnel. A funnel shape may improve flow into the angled lumen and may reduce the risk of clogging the angled lumen. The cross-sectioned assembled hemostasis valve 300 may be alternatively delineated as having a single distal channel and two proximal channels, wherein the single distal channel ends at the bifurcation 308 and the two proximal channels start at the bifurcation 308. With this expression, the distal channel extends the length 120 of the first fluid channel 103 and across a portion of the length 120 of the second fluid channel 110, and the proximal channels extend along the remaining length 120 of the second fluid channel 110, namely, upper lumen 309 and linear lumen 310. The second fluid channel 110 may include a ledge 115 that prevents the overtightening and over-loosening of an attached rotating locking mechanism. In FIG. 3, this ledge 115 is illustrated on the outer surface of the linear lumen 310 at a location immediately distal of the threads 114. The ledge 115 may interact with a distal ledge 311 of the proximal rotating locking mechanism 116 to prevent over-loosening of the proximal rotating locking mechanism 116. The ledge 115 may interact with a proximal ledge 312 of the proximal rotating locking mechanism 116 to prevent the overtightening of the proximal rotating locking mechanism 116. Typically, the ledges come into contact with one another as the proximal rotating locking mechanism 116 advances or retracts over the second fluid channel 110 as it is tightened or loosened by a user to open or close the seal 118, the seal stabilizer 119, or both, whereby contact between two ledges inhibits continued movement. The distal ledge 311 and the proximal ledge 312 may be at least semi-annular, wrapping around a perimeter of the inner surface of the proximal rotating locking mechanism 116. The distal ledge 311 may be flat and squared on a proximal side and rounded, curved, or slanted on a distal side. In some examples, the distal ledge 311 may have a fin shape as described earlier. The proximal ledge 312 may be flat and squared on a distal side. A complementary shape between the distal ledge 311, the proximal ledge 312, and the ledge 115 ensures that the proximal locking mechanism 116 can both be successfully attached to the second fluid channel 110, and that, once attached, the various ledges properly interact to prevent over tightening and over-loosening. For instance, a rounded or curved distal side of the distal ledge 311 may facilitate attachment to the second fluid channel 110 by allowing the distal ledge to more easily slide over the ledge 115 when the proximal locking mechanism 116 is attached to the second fluid channel 110, while a flat or right-angled proximal side of the distal ledge 311 may ensure that the proximal locking mechanism 116 cannot be easily removed from the second fluid channel 110 and a flat or right-angled proximal side of the distal ledge 311 may cause the proximal locking mechanism 116 to abruptly and securely when loosened. For similar reasons, the ledge 115 may be proximally flat or right angled and distally rounded or curved. The complimentary features both facilitate easy attachment and prevent accidental detachment.

Figure 4:
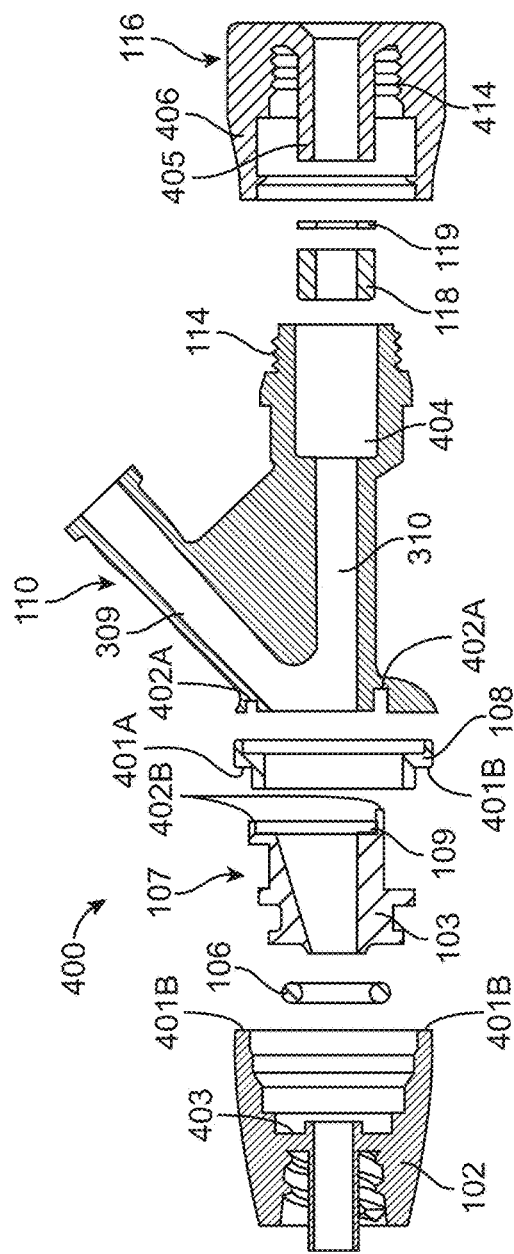
FIG. 4 illustrates an exploded, cross-sectioned hemostasis valve, and optional accessories.

FIG. 4 provides an illustration of an exploded, cross-sectioned hemostasis valve 400. From this perspective, one embodiment of the first fluid channel's 103 optional protrusion 109 may be either at least semi-annular in shape, extends across a width 121 of the first fluid channel 103, or both. The geometry of the protrusion 109 may facilitate a closed system by ensuring that the first fluid channel 103 is attached to the second fluid channel 110 in a proper orientation. In this example, the width 121 of the proximal opening 305 of the tapered lumen 303 is sized to match the width of the single distal opening 306 of the second fluid channel 110 to facilitate a smooth and continuous lumen between the two fluid channels. In some embodiments, all spatial geometries, such as an oblong, oval, or figure eight shape, of the proximal opening 305 of the tapered lumen 303 are sized to match the single distal opening 306 of second fluid channel 110. In some instances, the geometries of the lumens and their openings are optimized to direct flow into the upper lumen 309 or are optimized to direct flow along two paths, one path being into the upper lumen 309 and the other path being into the linear lumen 310.

FIG. 4 illustrates surfaces of the exploded cross-sectioned hemostasis valve 400 that are glued, press fit, or otherwise adhered to form an assembled hemostasis valve. In one method of construction, the O-ring 106 is positioned into an annular seat 403 of the distal rotating locking mechanism 102. A next step may be to position the floating latch 108 within the annular recession 107 of the first fluid channel 103. A next step may be to attach an annular surface 401A of the floating latch 108 to an annular surface 401B of the distal rotating locking mechanism 102. Generally, because of geometric constraints, the floating latch 108 must be attached before the first fluid channel 103 is attached to the second fluid channel 110. Once the floating latch 108, first fluid channel 103, and distal rotating locking mechanism 102 are attached, a distal structure is formed, which may be attached to the second fluid channel, e.g. a proximal structure. In one example, a next step may be to attach an at least semi-annular surface 402B of the protrusion 109 to the at least semi-annular surface 402A of the indent 304. This attachment may affect the interlocking of the protrusion 109 of the first fluid channel 103 and the indent 304 of the second fluid channel 110. In alternative embodiments, the first fluid channel 103 may have an indent and the second fluid channel 110 may have a protrusion or some other complimentary mating features. Additionally, the shapes of the protrusion and indents may vary from being semi-annular to completely annular, or to some other similar shape. The shapes preferably have a key and lock relation, whereby protrusions and indents ensure that the two channels can only be connected in a singular and proper orientation.

Once the first fluid channel 103 is fixedly adhered to the second fluid channel 110, a next step may be to place the seal 118 and seal stabilizer 119 inside a compartment 404 of the second fluid channel 110. The compartment 404 may represent an enlarged region of the linear lumen 310. The compartment 404 ensures that, even with the placement of the seal 118 and the seal stabilizer 119 within the linear lumen 310, the linear lumen 310 still maintains an effective cross-sectional area similar to or greater than 10F in diameter. To achieve this, the seal 118 and the seal stabilizer 119 may feature a lumen of at least 10F in diameter when uncompressed. The proximal rotating locking mechanism 116 is generally comprised of an inner cylinder 405 and an outer cylinder 406 that are attached at their bases. The outer cylinder 406 may include threads 414 that face inwards and are disposed in a proximal region of the outer cylinder 406. The threads 414 on the proximal rotating locking mechanism 116 are preferably complimentary in shape to the threads 114 on the second fluid channel 110. As the proximal rotating locking mechanism 116 engages the threads 114 of the second fluid channel 110, the inner cylinder 405 enters the compartment 404 and presses into the seal 118 and the seal stabilizer 119. When the proximal rotating locking mechanism 116 is loosely fitted, the linear lumen 310 of the second fluid channel 110 has an effective cross-sectional diameter equivalent to or greater than 10F in diameter from the distal end 111 of the second fluid channel 110 to the proximal end 117 of the proximal rotating locking mechanism 116. As the proximal rotating locking mechanism 116 is tightened, it is pulled deeper into the compartment 404 and begins to compress the seal 118 and the seal stabilizer 119. As the seals are compressed, their lumens begin to shrink. In practice this is useful when a catheter or guidewire is threaded through the linear lumen 310, because the tightening of the proximal rotating locking mechanism 116 compresses the seals and thereby effects a seal on the outside surface of whatever device is passing through the linear lumen 310. The seals and locking mechanism thereby facilitate hemostasis by preventing blood loss and air embolism through the hemostasis valve.

Figure 5:
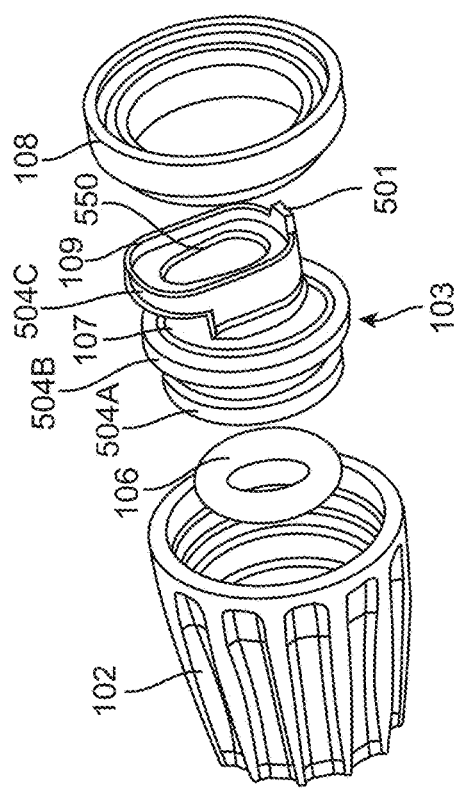
FIG. 5 illustrates an exploded, angled perspective of a fluid channel, a locking mechanism, and optional accessories.

FIG. 5 illustrates an exploded and angled perspective of the first fluid channel 103 and the distal rotating locking mechanism 102. This example illustrates the ridges on the outer surface of the distal rotating locking mechanism 102 that facilitate grip by a user's fingers and the many seats on the inner surface of the distal rotating locking mechanism 102 that facilitate the placement of the O-ring 106, the first fluid channel 103, and the floating latch 108. The first fluid channel 103 may include several annular ridges that are complementary in shape to the seats of the distal rotating locking mechanism 102. The annular ridges may act as rails that guide the smooth rotation of the distal rotating locking mechanism 102 over the first fluid channel 103. Typically, the distal rotating locking mechanism 102 spins freely over the first fluid channel 103 and locking is achieved by pulling a catheter or similar interventional device into the threads 302, which are not visible here. The first fluid channel 103 may include three annular ridges. In one example, the first fluid channel 103 includes a distal annular ridge 504A, an intermediate annular ridge 504B, and a proximal annular ridge 504C. The annular ridges may be entirely annular, wherein they wrap around the circumference of the outer surface of the first fluid channel 103, they may be semi-annular, wherein they wrap around only a portion of the circumference of the outer surface of the first fluid channel 103, or some annular ridges may be annular while others are semi-annular. In the example illustrated in FIG. 5, the distal annular ridge 504A and the intermediate annular ridge 504B are annular and the proximal annular ridge 504C is semi-annular. The ridges may have a variable height, a consistent height, a segmented series of different heights, or some combination thereof. The distal annular ridge 504A and the intermediate annular ridge 504B may provide rails for the distal rotating locking mechanism 102. The seats and annular ridges may have a consistent interface distance that permits smooth rotation of the distal rotating locking mechanism 102 over the annular ridges. In some instances, it may be preferable for the distal annular ridge 504A and the intermediate annular ridge 504B to be completely annular to facilitate a constant interface distance from the seats of the distal rotating locking mechanism 102, which will ensure smooth rotation of the distal rotating locking mechanism 102 over the first fluid channel 103. The intermediate annular ridge 504B and the proximal annular ridge 504C may form an annular recession 107 in the space between the two ridges that accommodates the floating latch 108. In some examples, it may be preferable for the proximal annular ridge 504C to be only semi-annular, which will allow the floating latch 108 to be advanced over the proximal end of the first fluid channel 103 into the annular recession 107. The proximal annular ridge 504C may include a protrusion 109. The protrusion 109 may be orientated as a sleeve around an outer perimeter of the proximal annular ridge 504C, wherein a thin band of material extrudes perpendicularly from the outer perimeter of the ridge in a proximal direction. The protrusion 109 may have an edge that is squared, rounded-squared, or the like. The protrusion 109 may include a peg 501 that extends further proximally than the rest of the protrusion 109. The peg 501 may be square, rectangular, polygonal, round, or some other similar shape. The peg 501 typically facilitates a key-and-lock feature between the first fluid channel 103 and the second fluid channel 110 (not shown here) by ensuring that the two components can only be fitted together in a singular and proper orientation. The indent 304 typically has a complimentary shape to both the protrusion 109 and the peg 501 to facilitate assembly in a proper orientation.

Figure 6:
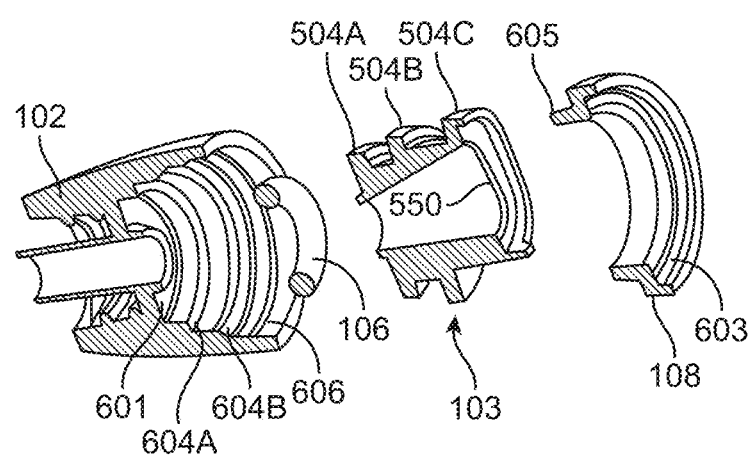
FIG. 6 illustrates an exploded, angled, and cross-sectioned perspective of a fluid channel, a locking mechanism, and optional accessories.

FIG. 6 illustrates an exploded, angled, and cross-sectioned perspective of the first fluid channel 103 and the distal rotating locking mechanism 102. This example illustrates one embodiment of the seats on the inner surface of the distal rotating locking mechanism 102. Near the center of the distal rotating locking mechanism 102 is an annular O-ring seat 601 that facilitates the placement of the O-ring 106. Moving proximally, distal rotating locking mechanism 102 includes a distal channel seat 604A and a proximal channel seat 604B, which both facilitate the positioning of the first fluid channel 103. Importantly, these channel seats enable the free rotation of the distal rotating locking mechanism 102 relative to the first fluid channel 103. In one example, the distal channel seat 604A is complimentary in shape to the distal annular ridge 504A and the proximal channel seat 604B is complimentary in shape to the intermediate annular ridge 504B. The distal rotating locking mechanism 102 may also include a floating latch seat 606 that is complimentary in shape to a protrusion 605 of the floating latch 108, wherein the protrusion 605 is fixedly attached to the floating latch seat 606 in an assembled device. The floating latch 108 may include an annular ridge seat 603 that is at least partially complimentary in shape to a distal side of the proximal annular ridge 504C. The annular ridge seat 603 may facilitate a consistent or constant interface distance between the floating latch 108 and the proximal annular ridge 504C, which will enable smooth rotation of the floating latch 108 relative to the second fluid channel 103.

Figure 7:
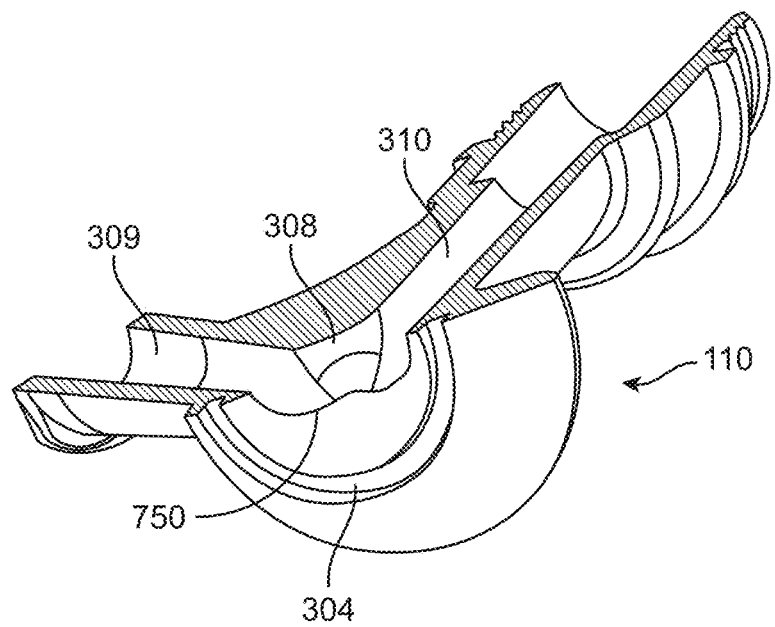
FIG. 7 illustrates an angled, cross-sectioned perspective of a fluid channel.

FIG. 7 illustrates an angled and cross-sectioned perspective of the second fluid channel 110. This perspective provides a clear view of one embodiment of the indent 304 of the second fluid channel 110. Here, the indent 304 is at least semi-annular and includes a squared edge at the bottom of the indent 304. The indent 304 may vary in depth along the circumference of the indent 304. A variable depth may enable a key-and-lock fit between the indent 304 and a compatible protrusion. Here, the indent 304 is on a surface that is perpendicular to the longitudinal axis of either the linear lumen 310, the upper lumen 309, or a median point between the two lumens. Additionally, the indent 304 may include a regression that is deeper than the rest of the indent 304 that accommodates a peg of a compatible structure. The regression may have a shape that is rectangular, round, squared, polygonal, or similar shape. In other embodiments, such an indent 304 is found on the first fluid channel 103 and the protrusion 109 illustrated on the first fluid channel 103 is present on the second fluid channel 110. From the orientation provided in FIG. 7, the upper lumen 309 is on the left and the linear lumen 310 is on the right. Between these two lumens is the bifurcation 308 from the single lumen 307 to the dual lumens. A surface of the bifurcation 308 may be set back from an intersection of the upper lumen 309 and linear lumen 310. A setback of the intersection between the upper lumen 309 and the linear lumen 310 provides the space necessary to allow a smooth and rounded bifurcation surface between the two channels. If this intersection was not set back, then a sharp edge would be present at this bifurcation, which could catch on or ensnare aspirated materials such as stringy or fibrous clot. In one example, the intersection is set back far enough to provide the space necessary for sufficient rounding, such that the rounding reduces or eliminates the chance that aspirated materials are caught or ensnared on the bifurcation surface. A smooth and rounded edge at the bifurcation 308 mitigates the risk of clogging when aspiration is applied to the upper lumen 309, lower lumen 310, or both. The bifurcation surface may have various geometries and shapes. In one example, the surface of the bifurcation 308 may have a generally hyperbolic paraboloid shape that presents a smooth and rounded edge as the second fluid channel 110 transitions from one to two lumens. Alternatively, the surface of the bifurcation 308 may have the shape of a conic section, such as an ellipse, parabola, or hyperbola, or some other similar shape. A distance between the intersection and the setback bifurcation surface may be equal to a diameter of the upper lumen 309 or the linear lumen 310. Alternatively, the intersection may be set back by a distance as little as one radius or to as great as the sum of three radius of either the upper lumen 309 or the linear lumen 310. Alternatively, the intersection may be set back by 5-15% of the length of the upper lumen 309 or linear lumen 310.

FIGS. 3 through 6 illustrate the tapered lumen 303 of the first fluid channel 103. The tapered lumen 303 allows for a larger internal volume along the hemostasis valve's flow path and the tapered lumen 303 may provide smooth flow and directionality into the upper lumen 309, the lower lumen 310, or both. In some examples, the tapered lumen 303 may include an inner surface with lines, veins, or rifling that help direct flow. In one specific example, the tapered lumen 303 features an inner surface with a cross-sectional circumference resembling the outline of a figure eight. An upper lobe of this shape may direct flow towards the upper lumen 309 while the lower lobe of this shape may direct flow towards the linear lumen 310. FIGS. 5 and 6 illustrate an example of this figure eight inner geometry 550 on the first fluid channel 103, while FIG. 7 illustrates a continuation of this figure eight inner geometry 750 into the second fluid channel 110. The large internal volume of the tapered lumen 303 necessarily increases the outer circumference of the first fluid channel 103. To utilize a distal locking mechanism 102 with an optimal size for facilitating usability, the outer geometries of the first fluid channel 103 are desirably configured to reduce the overall footprint of the attached distal locking mechanism 102. The footprint of the distal locking mechanism 102 is reduced by the annular recession 107 positioned near the widest region of the first fluid channel 103. This annular recession accommodates the placement of the floating latch 108, which provides a surface within the annular recession 107 that is freely rotatable and may be adhered to the distal locking mechanism 102. Without the annular recession 107 and the floating latch 108, the footprint of the first fluid channel 103 would be enlarged along its entire circumference by an amount equal to the depth of the annular recession 107. The annular recession 107 and the floating latch 108 work together to reduce the overall footprint of the hemostasis valve and improves usability. In one example, the proximal annular ridge 504C is only partially annular to ensure that the floating latch 108 can be advanced over the proximal annular ridge 504C before the floating latch is attached to the distal locking mechanism 102.

FIG. 8 illustrates an exploded perspective of a clamshell hemostasis valve 800. Such an embodiment may include a recession 801 comprised of a clamshell seat 807 and fluid beds 802 that include a bifurcation 803 from one fluid bed to two fluid beds. The bifurcation 803 provides a smooth and rounded surface as the fluid beds 802 bifurcate from one to two fluid beds. The fluid beds 802 are typically recessed lower than the clamshell seat 807. The fluid beds 802 typically have a cylindrical shape with a bottom and sidewalls, wherein the sidewalls end when their angle is approximately 90-degrees relative to the bottom of the fluid bed 802. The sidewalls end with a right-angled edge that marks the beginning of the clamshell seat 807. The clamshell seat 807 may be comprised of a squared edge, right-angled edge, or some similar shape that lines at least a portion of the perimeter of the fluid beds 802. In one example, the right-angled edge of the clamshell seat 807 is comprised of a first flat surface 808A, that is parallel relative to the bottom of the fluid beds 802, and a second flat surface 808B, that is perpendicular relative to the bottom of the fluid beds 802. The clamshell seat 807 typically accommodates a clamshell cap 901—illustrated in FIG. 9—that has a shape complimentary to the recession 801. When the clamshell cap 901 is positioned above the recession 801 the fluid beds 802 form a fluid channel, wherein the clamshell hemostasis valve 800 has a single opening on a distal end 804 and one opening on each of the two proximal ends 805. The proximal ends 805 may include threads 114 that allow for the attachment of rotating locking mechanisms. A proximal rotating locking mechanism 116 may be attached at both proximal ends 805. The proximal rotating locking mechanisms 116 may either accommodate the sealed insertion of guidewires and similar devices, facilitate the placement of additional catheters, facilitate the attachment of an aspiration source 806 or a fluid source, or some combination thereof. The clamshell hemostasis valve may include seals that facilitate the sealable insertion of coaxial devices. The distal end 804 may include threads or a snap fit feature to attach a distal rotating locking mechanism 809.

FIG. 9 illustrates an assembled perspective of a clamshell hemostasis valve 900. In such an embodiment, the boundaries of the fluid channel are defined by the fluid beds 802 of the recession 801 (fluid bed bottom) and fluid beds of the clamshell cap 901 (fluid bed top). The clamshell cap 901 includes fluid beds with a mirrored shape to the fluid beds 802 of the recession 801. The clamshell cap 901 may also include a squared edge that lines the perimeter of the clamshell cap 901 and has a shape that is complimentary to the clamshell seat 807 of the recession 801. When the clamshell cap 901 is placed on the recession 801 a sealed fluid channel is formed, wherein the fluid channel has at least nearly cylindrical lumens, a single distal opening, an internal bifurcation from one to two channels, and two proximal openings. The bifurcation may provide a generally hyperbolic paraboloid shaped edge between the two channels at the bifurcation 803.

In some embodiments, the hemostasis valve and the various components described herein and illustrated in the figures are manufactured via injection molding. The injection molding process may utilize molds, core pins, and molten polymer to manufacture components of a hemostasis valve. A mold provides the exterior structure and shapes for a component. The mold is typically filled with a molten polymer, which takes on the shapes and contours of the mold and then retains those shapes and contours once the polymer has cooled, hardened, and been removed from the mold. In some examples, the molds have a clamshell structure, whereby the molds are split in half to remove molded components. The molds typically include apertures through which core pins can be positioned at least partially within the mold. The core pins may shape internal geometries of the molded components, such as lumens, threads, ridges, cavities, and other similar structures. Any structural feature previously discussed or illustrated herein may have the corresponding structure necessary to form it appear in a mold or core pin. For instance, the ridges of a component may require cavities—or some other opposite or corresponding shape—in a mold or a core pin and vice versa. The present disclosure is intended to include all the molds and core pins necessary to form every hemostasis valve component detailed herein, even if the structures of the necessary molds and core pins are not explicitly detailed. Core pins may have a generally cylindrical or conical shape that may be positioned at least partially within a mold before molten polymer is poured into the mold. The core pins are removed from the mold once the molten polymer has cooled and hardened. Core pins typically require a draft angle that enables the removal of the core pin after the polymer has hardened. In general, the portion or the end of the pin that is positioned deepest in the component must be the narrowest portion or side of the pin. The pin then tapers or has a draft angle from this narrowest point or side along the length of the pin.

FIG. 10 illustrates examples of core pins that may be used to form the first fluid channel 103 and the second fluid channel 110. A tapered pin 1001 may be used to form a lumen for the first fluid channel 103. The tapered pin 1001 may have a distal end 1002 that is relatively narrow and a proximal end 1003 that is relatively wide, whereby the pin tapers or has a draft angle in a proximal to distal direction. The tapered pin 1001 may be generally cylindrical or conical along its length. The tapered pin 1001 may have a distal interface 1004 and a proximal interface 1005. The distal face 1004 and the proximal interface 1005 may have a flat surface and squared edges and a perimeter with a shape is that circular, oblong, or resembling a figure eight. The interfaces of all the pins may include locating features, such as a pin and hole or a peg and cavity to align and seal the mating interfaces of two pins with one another or to provide attachment structures for other components. In one example, the tapered pin 1001 forms the tapered lumen 303, the proximal opening 305, and a distal opening of the first fluid channel 103.

FIG. 10 also illustrates a hyperbolic paraboloid pin 1006, an upper pin 1007, and a linear pin 1008 that may be used to form the single lumen 307, upper lumen 309, the linear lumen 310, and the compartment 404 of the second fluid channel 110. The hyperbolic paraboloid pin 1006 may include three interfaces. A first interface 1009 may have a circular perimeter, a squared edge, and a flat surface that is perpendicular relative to the length of the linear pin 1008, whereby the first interface provides an interface between the hyperbolic paraboloid pin 1006 and the linear pin 1008. A second interface 1010 may have a circular perimeter, a squared edge, and a flat surface that is perpendicular relative to the first interface 1009, whereby the second 1010 interface provides an interface between the hyperbolic paraboloid pin 1006 and the upper pin 1007. A third interface 1011 may have a perimeter that is circular, oblong, or resembling a figure eight, a squared edge, and a flat surface that is perpendicular relative to the length of the linear pin 1008. The third interface 1011 may serve as a point of contact for pulling the hyperbolic paraboloid pin 1006 out of the mold once the polymer has hardened. The hyperbolic paraboloid pin 1006 may include a draft angle, where a distal end 1012 is relatively wide and a proximal end 1013 is relatively narrow, whereby the hyperbolic paraboloid pin 1006 gradually tapers, e.g. shrinks, in distal to proximal direction. The draft angle ensures that the pin is removable once the polymer hardens around it. The hyperbolic paraboloid pin 1006 includes a bifurcation surface 1014 with a hyperbolic paraboloid shape. The bifurcation surface 1014 sets back the natural intersection of the upper pin 1007 and the linear pin 1008 and forms a lumen with a rounded edge between the upper lumen 309 and the linear lumen 310. In one example, the hyperbolic paraboloid pin 1006 forms the single distal opening 306, the single lumen 307, and the bifurcation 308 of the second fluid channel 110.

The upper pin 1007 may be generally cylindrical or conical along its length and it may include two interfaces. A distal interface 1015 may be positioned on a distal end of the upper pin 1007, and the distal interface 1015 may have a circular perimeter, a squared edge, and a flat surface that is parallel to the second interface 1010 of the hyperbolic paraboloid pin 1006, whereby the distal interface 1015 provides an interface between the upper pin 1007 and the hyperbolic paraboloid pin 1006. A proximal interface 1016 may be positioned on a proximal end of the upper pin 1007, and the proximal interface 1016 may have a circular perimeter, a squared edge, and a flat surface that is perpendicular to the length of the upper pin 1007. The proximal interface 1016 may serve as a point of contact for pulling the upper pin 1007 out of the mold once the polymer has hardened. The upper pin 1007 may include a draft angle, where a distal end is relatively narrow and a proximal end is relatively wide, whereby the upper pin 1007 gradually tapers, e.g. shrinks, in a proximal to distal direction. The draft angle ensures that the pin is removable once the polymer hardens around it. In one example, the upper pin 1007 forms the upper lumen 309 of the second fluid channel 110.

The linear pin 1008 may be generally cylindrical or conical along its length and it may include three interfaces. A distal interface 1017 may be positioned on a distal end and may have a circular perimeter, a squared edge, and a flat surface that is perpendicular relative to the length of the linear pin 1008, whereby the distal interface 1017 provides an interface between the linear pin 1008 and the hyperbolic paraboloid pin 1006. An intermediate interface 1018 may be positioned at an intermediate position along the length of the linear pin 1008 and may have a circular perimeter, a rounded edge, and a flat surface that is parallel to the surface of the distal interface 1017. A proximal interface 1019 may be positioned on a proximal end and may have a circular perimeter, a squared edge, and a flat surface that is perpendicular relative to the length of the linear pin 1008. The proximal interface 1019 may serve as a point of contact for pulling the linear pin 1008 out of the mold once the polymer has hardened. The linear pin 1008 may include a draft angle, where a distal end is relatively narrow and a proximal end is relatively wide, whereby the linear pin gradually tapers, e.g. shrinks, in a proximal to distal direction. The draft angle ensures that the pin is removable once the polymer hardens around it. The draft angle of the linear pin may be maintained across a distal region 1020 and a proximal region 1021. The intermediate interface 1018 forms a distal surface of the proximal region 1021 that demarcates the stepped transition from the proximal region 1021 to the distal region 1020. In one example, the distal region forms the linear lumen 310 and the proximal region forms the compartment 404.

Figure 11:
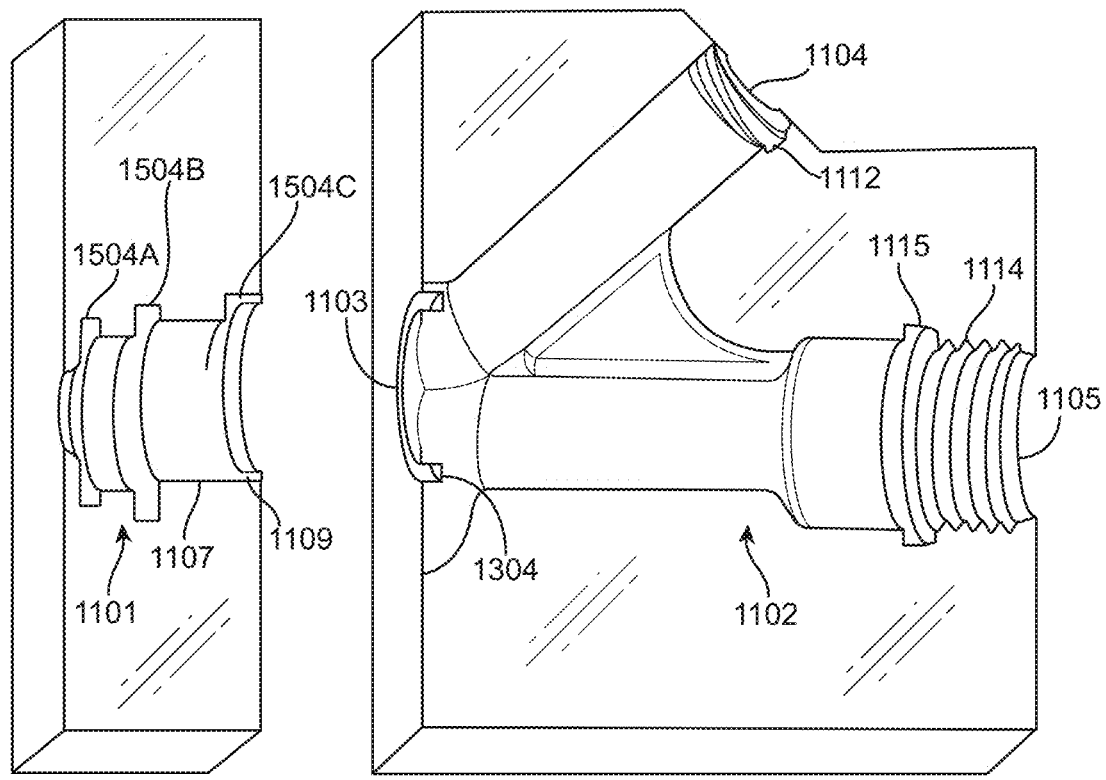
FIG. 11 illustrates cross-sectioned molds used for injection molding.

FIG. 11 illustrates cross-sections of molds that may be used to form the first fluid channel 103 and the second fluid channel 110. Such molds include internal cavities may be filled with a molten polymer, whereby the polymer takes on the shape of the mold and then retains that shape once it has cooled and hardened even after the polymer is removed from the mold. The molds may have a clamshell construction, whereby the molds can be split in two to allow molded components to be removed. A distal mold 1101 may comprise the shapes and geometries necessary to form a molded component with the shapes and geometries of the first fluid channel 103. For instance, the distal mold 1101 may include interior surfaces with the same shape as the outer surface of the first fluid channel 103. In one example, the distal mold 1101 may include grooves to form at least three at least semi-annular ridges around a perimeter of the tapered lumen 303. In another example, the distal mold 1101 may include a distal groove 1504A, an intermediate groove 1504B, a proximal groove 1504C, and a recession 1109, which provide the shape to, respectively, the proximal annular ridge 504A, intermediate annular ridge 504B, the distal annular ridge 504C, and the protrusion 109. The recession 1109 may include a region that is recessed deeper than the rest of the recession 1109, whereby this region facilitates the formation of the peg 501. The distal mold 1101 may also include a ridge 1107 that facilitates the formation of the annular recession 107. The distal mold may include a proximal opening that is larger than a distal opening. These openings may facilitate the insertion of a core pin, such as tapered pin 1001, in a proximal to distal direction. The molds of the present disclosure may include ridges, grooves, and recessions that surround or partially surround the interior perimeter of the mold with edges that may be squared, rounded, curved, angled, or some other similar shape.

FIG. 11 illustrates a proximal mold 1102 that may comprise the shapes and geometries necessary to form a molded component with the shapes and geometries of the second fluid channel 110. The proximal mold 1102 may include interior surfaces with the same shape as the outer surface of the second fluid channel 110. In one example, the proximal mold 1102 features grooves and ridges to form the ledge 115, threads 114, indent 304 and other structures of the second fluid channel 110. In another example, the proximal mold 1102 includes a first groove 1115, a second groove 1112, a series of ridges 1114, and a ridge 1304 to form, respectively, the ledge 115, the proximal end 112, the threads 114, and the indent 304 of the second fluid channel 110. The mold may include a distal opening 1103 configured for the removable insertion of the hyperbolic paraboloid pin 1006, an upper opening 1104 configured for the removable insertion of the upper pin 1007, and a proximal opening 1105 configured for the removable insertion of the linear pin 1008.

Figure 12:
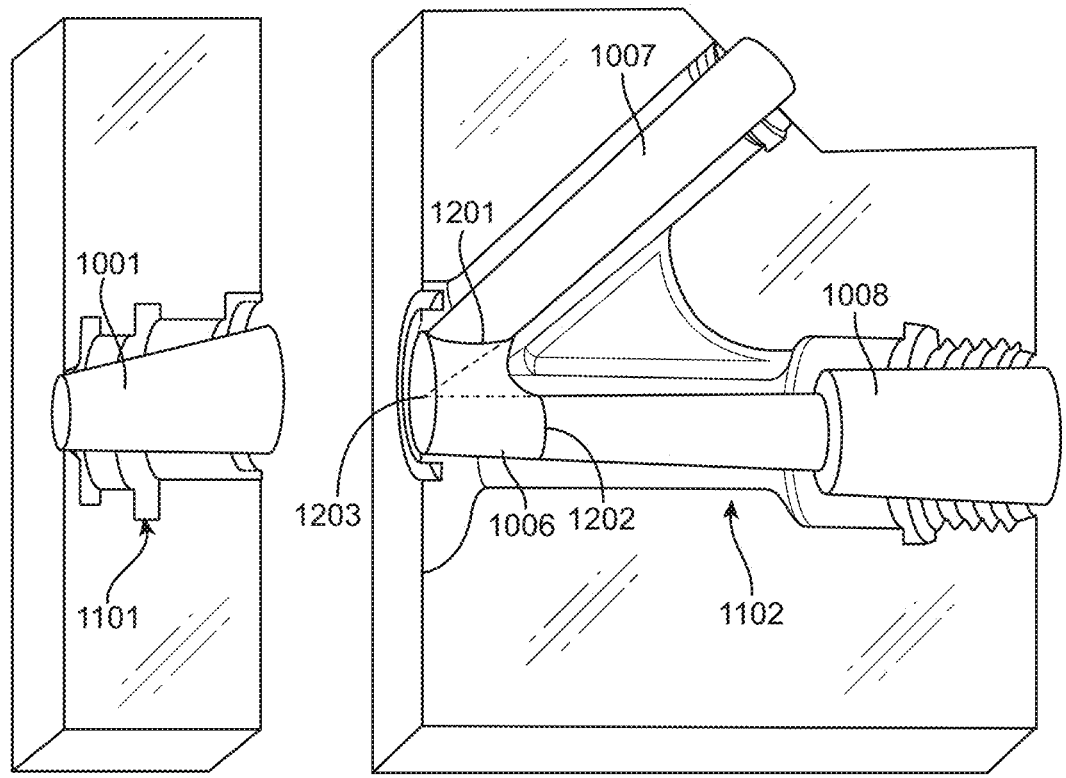
FIG. 12 illustrates core pins positioned within cross-sectioned molds.

FIG. 12 illustrates cross-sections of the molds with the pins positioned within the molds. In one example, the pins are positioned at least partially within a mold and then molten polymer is poured into the mold, whereby the molten polymer takes on the combined shapes of the mold and the pin(s). Once the polymer is cool and hardened, the pins may be removed and the component may be removed from the mold, whereby the component maintains the shape imparted on it by the pin(s) and the mold. In one example, a tapered pin 1001 is introduced into the distal mold 1101 in a proximal to distal direction. After the tapered pin 1001 is positioned within the mold, the mold may be filled with molten polymer. In this example, the distal mold 1101 imparts the exterior shape of the first fluid channel 103 onto the polymer and the tapered pin 1001 imparts the shape of the tapered lumen 303 onto the polymer. The combined mold, pin(s), and molten polymer are allowed to rest and cool. The tapered pin 1001 is then removed in a distal to proximal direction, i.e. according to its draft angle, and the mold is opened, e.g. along a clamshell half, and the molded component is removed and the molded component thereafter retains the shapes and geometries of the first fluid channel 103.

FIG. 12 illustrates an example where the hyperbolic paraboloid pin 1006 is introduced in a distal to proximal direction into the distal opening 1103 of the proximal mold 1102. The upper pin 1007 may be introduced in a generally proximal to distal direction into the upper opening 1104 of the proximal mold 1102. The linear pin 1008 may be introduced in a proximal to distal direction into the proximal opening 1105 of the proximal mold 1102. The second interface 1010 of the hyperbolic paraboloid pin 1006 may have an interface surface with complimentary geometries as the distal interface 1015 of the upper pin 1007. When the hyperbolic paraboloid pin 1006 and the upper pin 1007 are positioned within the proximal mold 1102, the second interface 1010 and the distal interface 1015 may form a seal at a first pin interface 1201, whereby molten polymer is excluded from between the second interface 1010 and the distal interface 1015 to allow a continuous lumen to be formed between the two pins in the finished molded component. The first interface 1009 of the hyperbolic paraboloid pin 1006 may have an interface surface with complimentary geometries as the distal interface 1017 of the linear pin 1008. When the hyperbolic paraboloid pin 1006 and the linear pin 1008 are positioned within the proximal mold 1102, the first interface 1009 and the distal interface 1017 may form a seal at a second pin interface 1202, whereby molten polymer is excluded from between the first interface 1019 and the distal interface 1017 to allow a continuous lumen to be formed between the two pins in the finished molded component. After the pins have been positioned within the mold, the mold may be filled with molten polymer. In this example, the proximal mold 1102 imparts the exterior shape of the second fluid channel 110 onto the polymer and the hyperbolic paraboloid pin 1006 imparts the shape of the single lumen 307 and the bifurcation 308, the upper pin 1007 imparts the shape of the upper lumen 309, and the linear pin 1008 imparts the shape of the linear lumen 310 and the compartment 404 onto the polymer. The combined mold, pins, and molten polymer are allowed to rest and cool. The hyperbolic paraboloid pin 1006 is then removed in a proximal to distal direction, i.e. according to its draft angle, and the upper pin 1007 and the linear pin 1008 are then removed in a distal to proximal direction, i.e. according to their draft angles, and the mold is opened, e.g. along a clamshell half, and the molded component is removed and the molded component thereafter retains the shapes and geometries of the second fluid channel 110.

The manufacturing of the second fluid channel 110 preferably utilizes the proximal mold 1102 and three separate pins. A manufacturing process for the second fluid channel 110 that only used two pins, e.g. longer versions of the upper pin 1007 and the linear pin 1008, would form a lumen that bifurcates with a pointed edge where these two pins intersect. FIG. 12 illustrates a projection of the upper pin 1007 and the linear pin 1008 with dotted lines that form a pointed edge 1203 at a natural intersection of these pins. A two-pin design cannot form a bifurcation with a rounded edge, because the pins must taper according to a draft angle and cannot have any flared or enlarged ends. Additionally, in a two-pin design, the draft angle of the upper pin 1007 would cause the opening into the upper lumen 309 to be the narrowest region of the upper lumen 1007. Both a narrow opening and sharp edges would negatively impact flow through the upper lumen 309. By introducing a third pin, i.e. the hyperbolic paraboloid pin 1006, the natural intersection depicted by pointed edge 1203 may be set back to the bifurcation surface 1014 of the hyperbolic paraboloid pin 1006. The setback of the natural intersection enables the formation of a lumen that bifurcates with a rounded edge. In particular, the bifurcation surface 1014 of the hyperbolic paraboloid pin 1006 enables the formation of a single lumen 307 that bifurcates with a hyperbolic paraboloid shape on the surface between the upper lumen 309 and the linear lumen 310.

Figure 13:
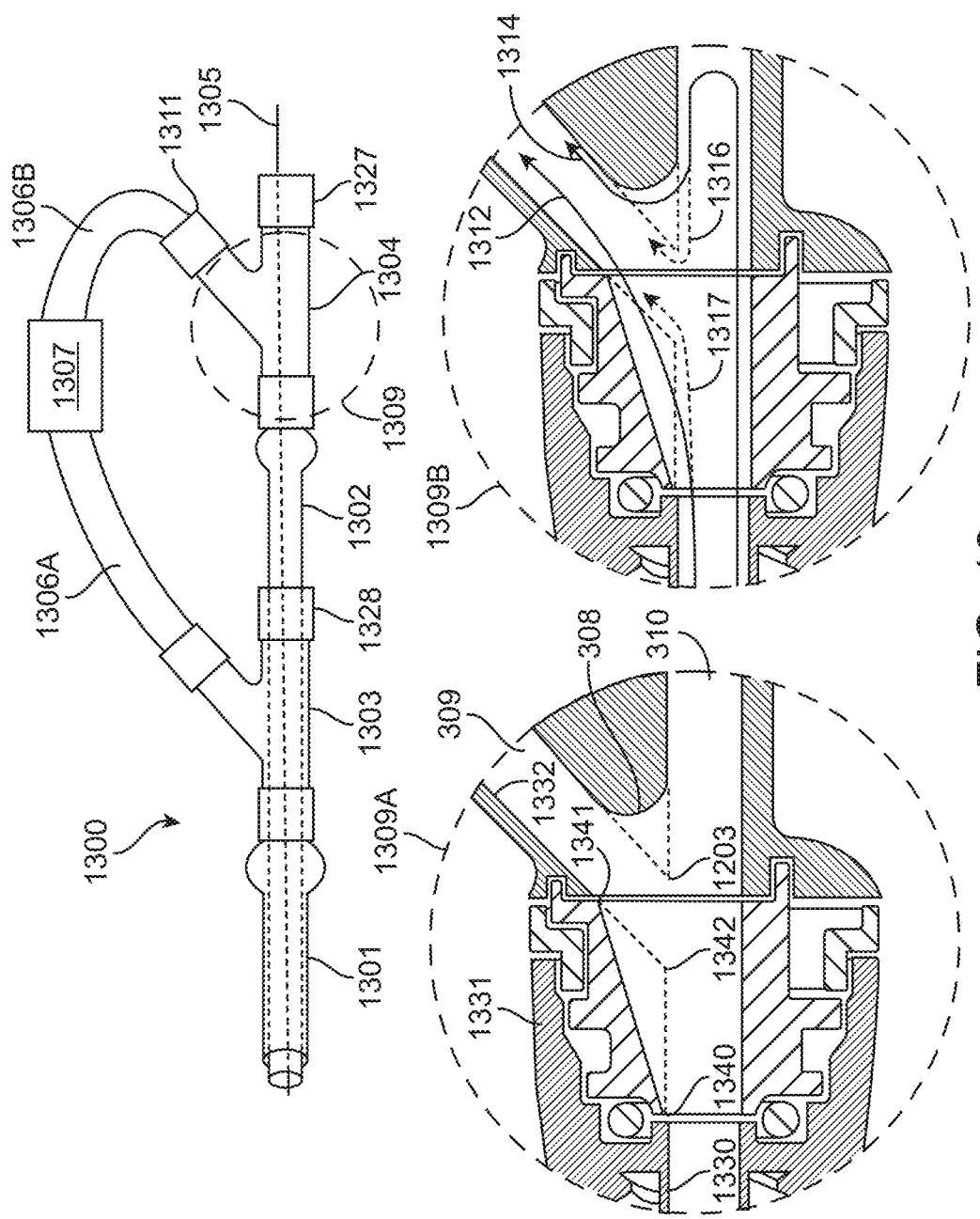
FIG. 13 illustrates a catheterization system and flow paths therein.

FIG. 13 illustrates a catherization system 1300 comprised of a large catheter 1301, a small catheter 1302, a first hemostasis valve 1303, a second hemostasis valve 1304, a guidewire 1305, connection tubing 1306A/1036B, and an aspiration source 1307. Such a system may be constructed to provide a closed system capable of safely assessing body lumens. A first step of constructing this catheterization system 1300 may be to connect the first hemostasis 1303 valve to the larger catheter 1301 and the second hemostasis valve 1304 to the small catheter 1302 by spinning the distal locking mechanisms of the hemostasis valves to pull the hubs of the catheters into the threads of the distal locking mechanisms. Then the guide wire 1305 may be axially translated thru lumens of the smaller catheter 1302 and the second hemostasis valve 1304. The proximal sealing mechanism 1327 of the second hemostasis valve 1304 may then be spun to create a seal around the outer surface of the guidewire 1305. The combined smaller catheter 1302 and guidewire 1305 may then be axially translated through the lumens of the larger catheter 1301 and the first hemostasis valve 1303. The proximal sealing mechanism 1328 of the first hemostasis valve 1303 may then be spun to create a seal around the outer surface of the smaller catheter 1302. Connection tubing 1306A/1306B may be attached to one or both hemostasis valves to provide fluid injection or suction as needed. For instance, the connection tubing 1306A/1306B may attach the upper lumens of the hemostasis valves to one or more aspiration sources 1307 or a fluid source (not illustrated here). This catherization system 1300 may be used to navigate to a body lumen, such as an intravascular target. Once a catheter of the catherization system 1300 has reached the target, fluid, suction, or both may be provided to the target. If the target is in smaller anatomy, the guidewire 1305 may be removed from the catherization system 1300 and suction, fluid, or both may then be provided through the connection tubing 1306B attached to the second hemostasis valve 1304 through the smaller catheter 1302 to the target. If the target is in larger anatomy, then the guidewire 1305 and the smaller catheter 1302 may both be removed from the catherization system 1300 and suction, fluid, or both may be provided through the connection tubing 1306A attached to the first hemostasis valve 1303 through the larger catheter 1301 to the target. Clearing a catheter's lumen of other devices may beneficially enhance the flow generated by any applied suction or fluid. Additionally, a setback bifurcation that provides a rounded edge between upper lumens and linear lumens and a tapered distal lumen enhance flow through the catherization system 1300.

FIG. 13 illustrates a zoomed-in perspective 1309A that provides a close-up view of the internal geometries of the second hemostasis valve 1304. In some examples, the second hemostasis valve 1304 has the same features and connections as the assembled hemostasis valve 300 illustrated in FIG. 3. The zoomed-in perspective 1309A illustrates the second hemostasis valve 1304 without any catheter or guidewire positioned within its lumen. The second hemostasis valve 1304 is attached to a catheter on a distal end 1310 and to an aspiration source on a proximal end 1311 of the upper lumen 309. A proximal end of the linear lumen 310 is typically sealed by the seal 118 during aspiration. Once the attached catheter is positioned in the target, aspiration may be applied from the aspiration source 1307 through the upper lumen 309 of the hemostasis valve. Vacuum aspiration evacuates all of the spaces with the catherization system 1300. In this example, aspiration causes fluid to flow from both the catheter and the linear lumen 310 into the upper lumen 309, where it can be collected. To remove fluid from the target, such as blood clots or other stingy and globular material, the aspiration must draw the blood clots through the catheter and the upper lumen 309 into the connection tubing 1306B, where the blood clots can be collected and examined.

As depicted in zoomed-in perspective 1309A with solid lines, the internal geometries of the second hemostasis valve 1304 may be optimized to enhance flow into the upper lumen 309. The opening to the upper lumen 309 includes a distal side and a proximal side. The distal side of the opening to the upper lumen 309 may include a two-step transition that shortens the flow path from the catheter into the upper lumen and allows the flow to proceed along a smooth and gradual arc. For a first step of the transition, a linear surface 1330 transitions with a first angle 1340 into a first tapered surface 1331. For a second step of the of the transition, the first tapered surface 1331 transitions with a second angle 1341 into a second tapered surface 1332. As illustrated in FIG. 13, the first step of the transition is positioned immediately after a lumen of the distal rotating locking mechanism 102 while the second step of the transition is positioned immediately after a proximal end of the distal rotating locking mechanism 102. This two-step transition is enabled by the tapered lumen 303 of the first fluid channel 103, which allows the lumen of the hemostasis valve to gradually increase in volume from the end of the distal locking mechanism 102 to the bifurcation surface 308, which avoids undesirable bottlenecks in flow. The first angle 1340 is beneficially positioned immediately after the linear lumen 301 of the distal locking mechanism 102, which allows fluid to flow in the direction of the upper lumen 309 immediately. In some embodiments, the distal side of the opening to the upper lumen 309 may feature more than two transition steps. Where the two-step transition enhances flow into the upper lumen 309 on the distal side of the opening into the upper lumen 309, the setback bifurcation surface 308 enhances flow into the upper lumen 309 on the proximal side of the opening into the upper lumen 309. A setback of the natural intersection of the upper pin 1007 and the linear pin 1008, as detailed in the present disclosure's three-pin design, enables a setback bifurcation 308 that provides a curved surface between the upper lumen 309 and the linear lumen 310 and a wider opening into the upper lumen 309. In one example, the distal side of the opening into the upper lumen 309 is positioned at an intermediate or central location along the length of the second hemostasis valve 1304. Together, the setback bifurcation 308 and the two-step transition function as a funnel for the upper lumen 309. This funnel provides a wide opening into the upper lumen 309 with smooth and rounded edges that improve flow into the upper lumen 309 and reduces the risk of clogging as compared to a hemostasis valve lacking similar geometries on the proximal and distal side of the opening of the upper lumen 309.

Also depicted in zoomed-in perspective 1309A with dotted lines is an example of the internal geometries of a hemostasis valve manufactured with a two-pin design. The opening to the upper lumen 309 includes a distal side and a proximal side. In this example, the distal side of the opening to the upper lumen 309 includes a single-step transition from a linear flow path into an angled flow path of the upper lumen 309. In this example, the flow path is linear beyond the distal locking mechanism into a portion of the first fluid channel 103. This linear flow path than diverges according to a single angle 1342 towards the upper lumen 309. The single angle 1342 is positioned on a distal side of the opening to the upper lumen 309. The proximal side of the opening to the upper lumen 309 includes a pointed edge 1203 at the linear intersection of the upper lumen 309 and the linear lumen 310. Together, the single angle 1342 and the pointed edge 1203 form a narrow opening into the upper lumen 309 that is gated by two sharp angles. These features restrict flow and increase the risk of clogging relative to the funnel shaped opening of the prior example. These features may be especially problematic when aspirating globular, stringy, and irregular shaped material, such as blood clots, which may be especially susceptible to clogging the narrow opening and catching on the sharp angles.

FIG. 13 illustrates a second zoomed-in perspective 1309B that provides a close-up view of the fluid paths within the second hemostasis valve 1304 when aspiration is applied to the upper lumen 309. The fluid paths are shown in both solid and dotted lines. The solid lines illustrate flow paths enabled by the optimized geometry, and the dotted lines illustrate flow paths within a hemostasis valve having a two-pin design. The two-step transition on the distal side of the opening to the upper lumen 309 enables an optimized flow path 1312. The optimized flow path 1312 gradually arcs from the distal locking mechanism 102 to the upper lumen 309. The distance traveled by the optimized flow path 1312 is shorter than the first angled flow path 1317. The first angled flow path 1317 travels a greater linear distance and traverses a sharper angle before entering the upper lumen 309, as compared to the optimized flow path 1312. The sharper angle of the angled flow path 1317 may result in increased pressure drops as the flow loses kinetic energy traversing the sharp angle. Flow along the angled flow path 1317 is therefore more restricted than flow along the optimized flow path 1312. Where the two-step transition optimizes flow on the distal side of the opening to the upper lumen 309, the setback bifurcation surface optimizes flow on the proximal side of the opening to the upper lumen 309. The aspiration source 1307 provides suction through the upper lumen 309 to both the attached catheter 1302 and the linear lumen 310. Once the linear lumen 310 is evacuated, it forms an evacuated chamber adjacent to the optimized flow path 1312. The evacuated chamber facilitates the formation an alternate fluid path 1314 that flows through the linear lumen 310 before passing into the upper lumen 309. The alternate fluid path beneficially flows along the smooth and rounded bifurcation surface 308. The distance traveled by the alternate flow path is shorter than the distance traveled by a second angled flow path 1316. The second angled flow path traverses a very sharp and pointed angle 1203 before entering the upper lumen 309. The longer flow path and the sharper angle of the second angled flow path is more restrictive of flow than the alternate flow path 1314 that flows along the bifurcation surface 308. The optimized flow path 1312 and the alternate flow path 1314 are enabled by the optimized geometries of the second hemostasis valve 1304. The flow directing geometries of the present disclosure may direct flow into two separate lumens without creating a bottleneck. The optimized flow path 1312 and the alternate flow path 1314 may flow according to a funnel geometry at all sides of the opening to the upper lumen 309.

The clamshell hemostasis valve illustrated in FIGS. 8 and 9 may be manufactured according to a different protocol than that illustrated in FIG. 12. The clamshell hemostasis valve may be manufactured as two halves of a hemostasis valve, i.e. split down the middle, and those two halves may be later attached in a clamshell manner. Each half of clamshell hemostasis valve may be shaped in its own mold. These molds are filled with molten polymer, the polymer is allowed to cool, the molds are opened, and the resulting components are removed. Two components, one from each mold, are then combined together to form the fluid channels of the hemostasis valve. In some examples, the molds of the clamshell hemostasis valve do not require core pins to form lumens. Instead, the lumens are formed in halves in each of the molds. This manufacturing process may beneficially allow greater customization over the shapes and geometries of the lumens of the hemostasis valve.

While a number of preferred embodiments of the disclosure and variations thereof have been described in detail, other modifications and methods of using and medical applications for the same will be apparent to those of skill in the art. Accordingly, it should be understood that various applications, modifications, and substitutions may be made of equivalents without departing from the spirit of the disclosure or the scope of the claims.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the invention and that methods and structures within the scope of these claims and their equivalents be covered thereby.

What is claimed is:

1. A hemostasis valve, comprising:
   a sealable fluid channel that bifurcates from a single distal channel into two proximal channels; and
   a bifurcation surface,
   wherein the bifurcation surface defines an interior space formed between the two proximal channels,
   wherein the bifurcation surface is set back proximally a distance from an intersection of the two proximal channels, and
   wherein the sealable fluid channel is configured to accommodate the insertion of catheters and guidewires.

2. The hemostasis valve of claim 1, wherein the bifurcation surface between the two proximal channels has a smooth and rounded edge.

3. The hemostasis valve of claim 2, wherein the bifurcation surface has a hyperbolic paraboloid shape.

4. The hemostasis valve of claim 1, wherein at least one of the proximal channels includes a first portion of a funnel section, and the single distal channel includes a second portion of the funnel section.

5. The hemostasis valve of claim 4, wherein the funnel section is formed at a location where the single distal channel bifurcates into the two proximal channels.

6. The hemostasis valve of claim 5, wherein the second portion of the funnel section has a smaller effective cross-sectional area than the first portion of the funnel section.

* * * * *